(12) United States Patent
Takamatsu et al.

(10) Patent No.: US 10,341,536 B2
(45) Date of Patent: *Jul. 2, 2019

(54) IMAGING DEVICE, CONTROL METHOD THEREFOR, AND IMAGING SYSTEM

(71) Applicant: FUJIFILM Corporation, Tokyo (JP)

(72) Inventors: Masaki Takamatsu, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 171 days.

This patent is subject to a terminal disclaimer.

(21) Appl. No.: 14/945,662

(22) Filed: Nov. 19, 2015

(65) Prior Publication Data

US 2016/0156814 A1 Jun. 2, 2016

(30) Foreign Application Priority Data

Nov. 28, 2014 (JP) .................................. 2014-241019

(51) Int. Cl.
*H04N 5/04* (2006.01)
*G01N 21/64* (2006.01)
(Continued)

(52) U.S. Cl.
CPC ............... *H04N 5/04* (2013.01); *G01J 3/027* (2013.01); *G01J 3/0208* (2013.01);
(Continued)

(58) Field of Classification Search
CPC ...................................................... H04N 5/04
(Continued)

(56) References Cited

U.S. PATENT DOCUMENTS 7,145,681 B2 * 12/2006 Kato .................. H04N 1/00204
358/1.15
2006/0241868 A1 * 10/2006 Sun ......................... G06F 19/28
702/19
(Continued)

FOREIGN PATENT DOCUMENTS

EP          2 857 842 A1    4/2015
JP       2009-199194 A      9/2009
(Continued)

OTHER PUBLICATIONS

European Search Report dated Mar. 2, 2016 issued in corresponding Application No. 15194473.3.
(Continued)

*Primary Examiner* — Jefferey F Harold
*Assistant Examiner* — Justin B Sanders
(74) *Attorney, Agent, or Firm* — Birch, Stewart, Kolasch & Birch, LLP

(57) ABSTRACT

Disclosed are an imaging device, a control method therefor, and an imaging system capable of allowing efficient use by multiple users and achieving improvement of a rate of operation. An imaging device which photoelectrically reads fluorescence or chemiluminescence emitted from an object to image the object includes a control unit which receives first control information for controlling a first function and second control information for controlling a second function from a plurality of external terminals and performs control based on the received first and second control information. The control unit recognizes the execution states of the first function and the second function in each external terminal based on the first and second control information output from each external terminal, restricts simultaneous processing of the first function in the plurality of external terminals,
(Continued)

and performs parallel processing of the first function and the second function in the plurality of external terminals.

21 Claims, 9 Drawing Sheets

(51) Int. Cl.
      *G01N 21/76*     (2006.01)
      *G01J 3/02*      (2006.01)
      *G01J 3/44*      (2006.01)
      *G01N 35/00*     (2006.01)

(52) U.S. Cl.
      CPC ........... *G01J 3/0237* (2013.01); *G01J 3/0264* (2013.01); *G01J 3/0291* (2013.01); *G01J 3/4406* (2013.01); *G01N 21/6456* (2013.01); *G01N 21/76* (2013.01); *G01J 3/44* (2013.01); *G01N 35/00871* (2013.01)

(58) Field of Classification Search
      USPC ........................................................ 348/500
      See application file for complete search history.

(56) References Cited

U.S. PATENT DOCUMENTS

| | | | | |
|---|---|---|---|---|
| 2010/0302571 | A1* | 12/2010 | Inoue | G06F 3/1205 358/1.13 |
| 2011/0042213 | A1 | 2/2011 | Updyke et al. | |
| 2011/0223580 | A1 | 9/2011 | Kuwano et al. | |
| 2013/0070110 | A1 | 3/2013 | Yamaguchi | |
| 2014/0033274 | A1* | 1/2014 | Okuyama | H04L 63/10 726/3 |
| 2014/0157875 | A1* | 6/2014 | Yamamoto | G01N 30/86 73/53.01 |
| 2015/0125961 | A1 | 5/2015 | Goemann-Thoss et al. | |

FOREIGN PATENT DOCUMENTS

| | | | | |
|---|---|---|---|---|
| JP | 2010-241099 A | | 10/2010 | |
| JP | 2011-185821 A | | 9/2011 | |
| JP | 2013-502597 A | | 1/2013 | |
| JP | 2013-68725 A | | 4/2013 | |
| JP | 2013-165328 A | | 8/2013 | |
| JP | 2014-10136 A | | 1/2014 | |
| JP | 2014-44046 A | | 3/2014 | |
| JP | 2014044046 A | * | 3/2014 | ....... G01N 35/00871 |

OTHER PUBLICATIONS

Official Communication issued in corresponding European Application No. 15194473.3 dated May 17, 2017.

Japanese Notification of Reasons for Refusal and English translation for corresponding Japanese Application No. 2014-241019, dated Jan. 16, 2018.

Japanese Notification of Reasons for Refusal for corresponding Japanese Application No. 2014-241019, dated May 8, 2018, with Machine translation.

* cited by examiner

IMAGING DEVICE, CONTROL METHOD THEREFOR, AND IMAGING SYSTEM

CROSS-REFERENCE TO RELATED APPLICATIONS

The present application claims priority under 35 U.S.C. § 119 to Japanese Patent Application No. 2014-241019, filed on Nov. 28, 2014. Each of the above application(s) is hereby expressly incorporated by reference, in its entirety, into the present application.

BACKGROUND OF THE INVENTION

1. Field of the Invention

The present invention relates to an imaging device, a control method therefor, and an imaging system which photoelectrically read fluorescence or chemiluminescence emitted from an object to image the object.

2. Description of the Related Art

Hitherto, imaging devices in which an object is arranged in a housing and which irradiates with light using a light source provided in the housing to image the object have been used in various fields. Among such imaging devices, an imaging device which selectively uses an imaging method primarily according to the type of object, and images chemiluminescence, fluorescence, or reflected light from an object, or transmission light transmitted through the object by an imaging element to generate an image has been disclosed.

In many cases, such an imaging device is thus installed as common equipment in a research facility, and is shared and used by multiple users. For example, JP2014-010136A discloses a system in which an imaging device is used by multiple users, and suggests that, when there are use requests for the imaging device from multiple users, imaging processing or image analysis processing is performed according to the use request of each user according to a priority set in advance.

SUMMARY OF THE INVENTION

However, for example, when imaging chemiluminescence or fluorescence, or the like, since chemiluminescence or fluorescence emitted from the object is feeble, the imaging time (exposure time) may be extended, and analysis processing of the captured image may take a long time.

In such a case, as described in JP2014-010136A, if the processing of each user is performed in order in a time-division manner, the next user is kept waiting a long time, and the use efficiency of the imaging device is extremely poor.

JP2010-241099A discloses that, in a system where a plurality of multi-function machines are connected to a computer, the use situation of peripheral devices of other multi-function machines are displayed on a user interface screen of one multi-function machine; however, there is no disclosure of a method which allows efficient use of the above-described imaging device by multiple users.

JP2013-165328A discloses that, in a multi-function machine accessible from multiple users, a function setting item which is set by a predetermined user cannot be set by other users; however, there is no disclosure of a method which allows efficient use of the above-described imaging device by multiple users.

An object of the invention is to provide an imaging device, a control method therefor, and an imaging system capable of allowing efficient use by multiple users and achieving improvement of a rate of operation, in consideration of the problems described above.

An imaging device of the invention which photoelectrically reads fluorescence or chemiluminescence emitted from an object to image the object includes a control unit which receives first control information for controlling a first function and second control information for controlling a second function from a plurality of external terminals and performs control based on the received first and second control information, and a terminal recognition unit which recognizes a plurality of external terminals. The control unit recognizes the execution states of the first function and the second function by each external terminal based on the first and second control information output from each external terminal, restricts simultaneous processing of the first function by the plurality of external terminals, and performs parallel processing of the first function and the second function by the plurality of external terminals.

In the imaging device of the invention, it is preferable that the first function is an imaging function, and the second function is an analysis function of an image acquired by imaging.

The control unit may receive third control information for controlling a file operation function as a third function from each external terminal, may recognize the execution states of the first function and the third function by each external terminal, and may perform parallel processing of the first function and the third function by the plurality of external terminals.

The control unit may perform control such that only a function which is not controlled by other external terminals is executable by each external terminal.

The control unit may output information representing the execution states of the functions of the imaging device by other external terminals to each external terminal.

The control unit may receive execution reservation information of the first function from external terminals other than an external terminal, by which the first function is executed, and may execute the first function in the order of reception of the execution reservation information.

A control method for the imaging device of the invention which photoelectrically reads fluorescence or chemiluminescence emitted from an object to image the object includes, when receiving first control information for controlling a first function of the imaging device and second control information for controlling a second function of the imaging device from a plurality of external terminals and performing control of the imaging device based on the received first and second control information, recognizing the execution states of the first function and the second function by each external terminal based on the first and second control information output from each external terminal, and restricting simultaneous processing of the first function by the plurality of external terminals and performing parallel processing of the first function and the second function by the plurality of external terminals.

An imaging system of the invention includes the above-described imaging device of the invention, and the plurality of external terminals. Each external terminal includes an imaging, device recognition unit which recognizes the imaging device and acquires execution information of the functions of the imaging device from the imaging device.

In the imaging system of the invention, a plurality of imaging devices may be provided, each external terminal may include an imaging device information storage unit which stores registration information of the plurality of imaging devices, and the imaging device recognition unit may recognize the plurality of imaging devices based on the registration information and may acquire the execution information of the functions of each imaging device.

Each external terminal may include a display control unit which displays information of the execution states of the functions of the imaging device.

When the first function of the imaging device is being executed, the display control unit of each of external terminals other than the external terminal, in which the first function is being executed, may display information indicating that the first function is being executed.

According to the imaging device, the control method therefor, and the imaging system of the invention, since the control unit of the imaging device recognizes the execution states of the first function and the second function by each external terminal based on the first and second control information output from the external terminal, restricts simultaneous processing of the first function by the plurality of external terminals, and performs parallel processing of the first function and the second function by the plurality of external terminals, the first function can be performed sequentially for each external terminal, and the second function can be performed in parallel by external terminals other than the external terminal, by which the first function is being executed. Therefore, it is possible to allow efficient use of the imaging device by multiple users and to achieve improvement of the rate of operation.

DESCRIPTION OF THE PREFERRED EMBODIMENTS

Figure 1:
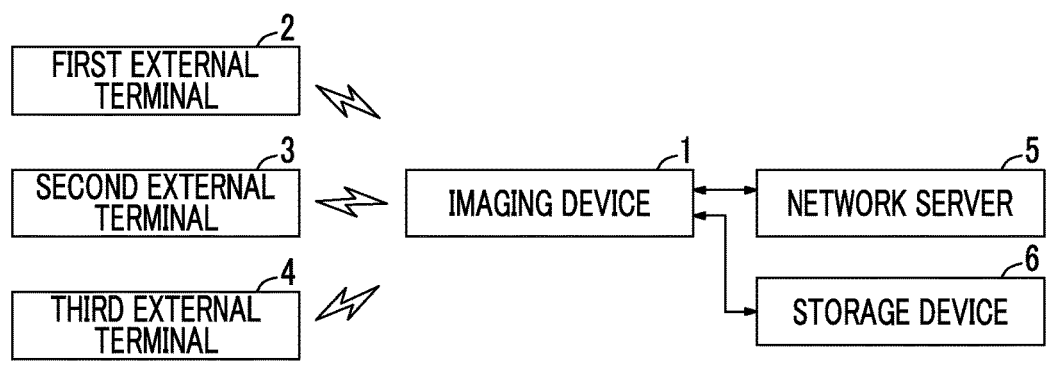
FIG. 1 is a block diagram showing the schematic configuration of an imaging system using an embodiment of an imaging device of the invention.
Figure 2:
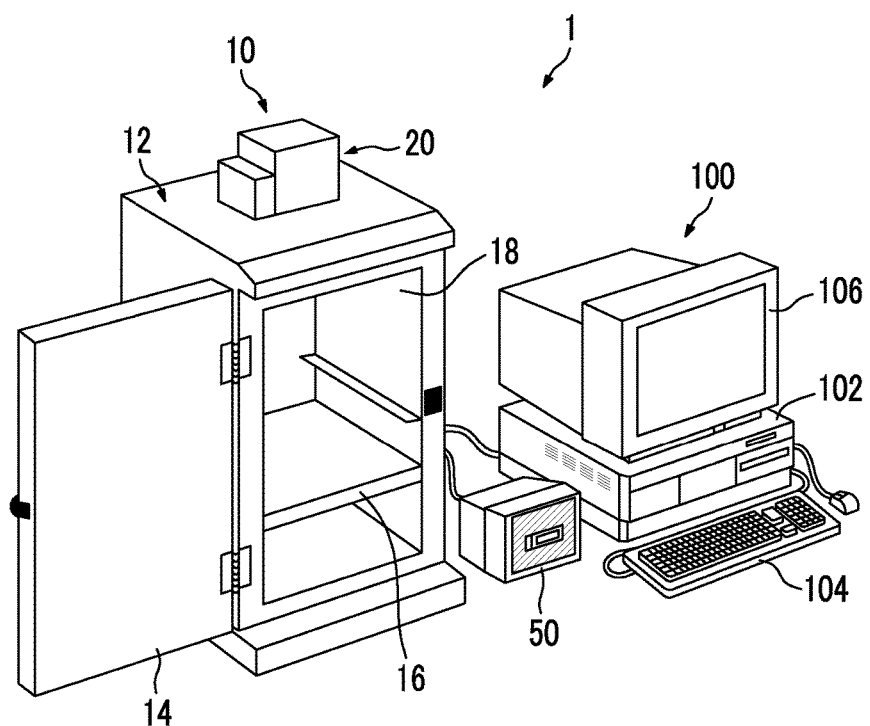
FIG. 2 is a schematic perspective view of the imaging device in the imaging system shown in FIG. 1.
Figure 3:
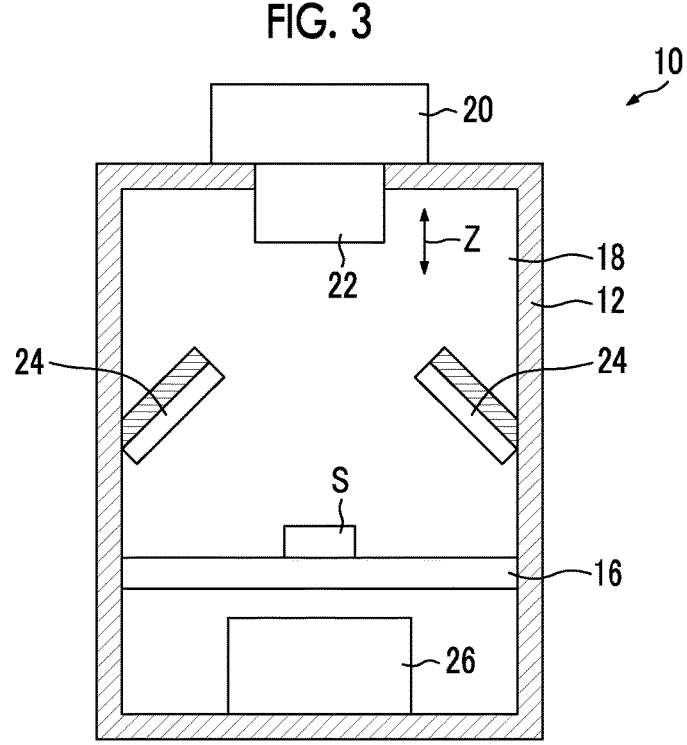
FIG. 3 is a schematic sectional view showing the internal configuration of the imaging device in the imaging system shown in FIG. 1.
Figure 4:
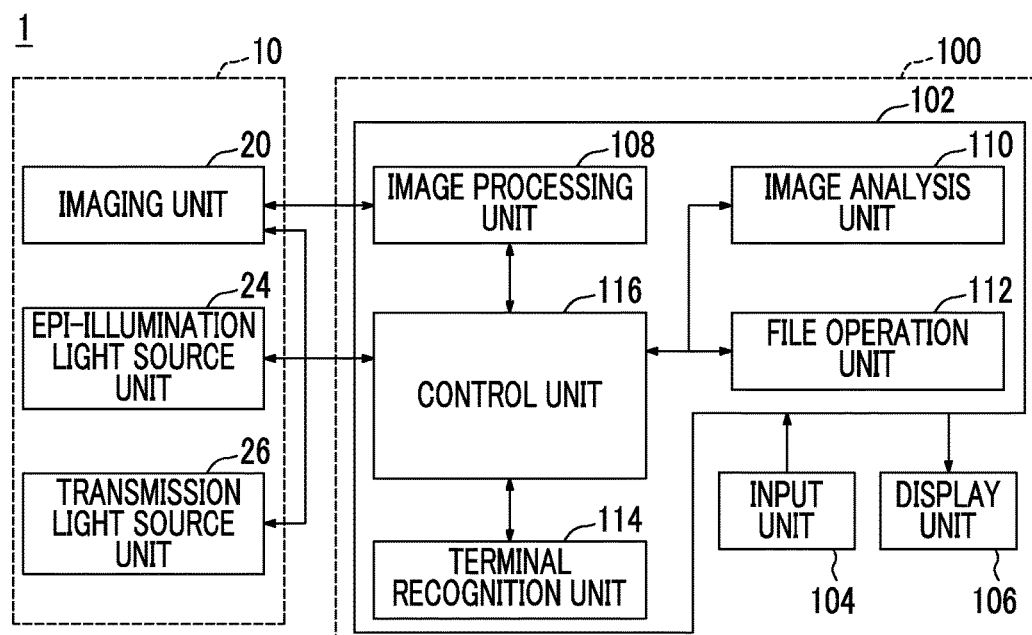
FIG. 4 is a block diagram showing the schematic configuration of the imaging device in the imaging system shown in FIG. 1.

Hereinafter, an imaging system using at embodiment of an imaging device and method of the invention will be described in detail referring to the drawings. FIG. 1 is a block diagram showing the schematic configuration of an imaging system of this embodiment, and FIG. 2 is a perspective view showing the schematic configuration of an imaging device in the imaging system shown in FIG. 1, FIG. 3 is a sectional view showing the internal configuration of an imaging device body shown in FIG. 2, and FIG. 4 is a block diagram showing the schematic configuration of the imaging device shown in FIG. 2.

As shown in FIG. 1, the imaging system of this embodiment includes an imaging device 1, first to third external terminals 2 to 4, a network server 5, and a storage device 6.

The imaging device 1 photoelectrically reads fluorescence or chemiluminescence emitted from an object placed in the imaging device 1 to image the object, and the first to third external terminals 2 to 4 output control information to the imaging device 1 and control the imaging function and the like of the imaging device 1. The imaging device 1 of this embodiment operates based on the control information output from the first to third external terminals 2 to 4, that is, is shared and used by multiple users.

The network server 5 and the storage device 6 temporarily store an electronic file (hereinafter, simply referred to as a file) including an image captured by the imaging device 1.

First, the imaging device 1 will be described in detail. As shown in FIGS. 2 and 3, the imaging device 1 includes an imaging device body 10 and an imaging control device 100.

The imaging device body 10 includes a housing 12 having a door 14, a stage 16 on which an object S is placed, an imaging unit 20, a lens unit 22, an epi-illumination light source unit 24, a transmission light source unit 26, and an object observation monitor 50.

The housing 12 has a hollow portion 18 formed in a substantially rectangular parallelepiped, and constitutes a black box where external light does not enter the hollow portion 18. The stage 16 on which the object S is placed is provided inside the housing 12. The door 14 shown in FIG. 2 is openably attached to the housing 12, and a user opens the door 14, places the object S on the stage 16, and then closes the door 14, thereby storing the object S in the housing 12. The stage 16 is formed of a material which transmits light from the transmission light source unit 26.

The imaging unit 20 is fixed to the top surface of the housing 12, includes, for example, an imaging element, such as a cooling charge coupled device (CCD) image sensor or a complementary metal-oxide semiconductor (CMOS) image sensor, and detects light reflected from the object S, fluorescence or chemiluminescence emitted from the object S, and light transmitted through the object S to generate an image signal. The image signal generated in the imaging unit 20 is subjected to, for example, amplification processing and is then output to the imaging control device 100.

The lens unit 22 is attached to the imaging unit 20. The lens unit 22 includes, for example, a plurality of lenses, and the lenses are provided movably in an arrow Z direction in order to focus on the object S. The lens unit 22 includes, for example, optical elements, such as a diaphragm and an excitation light cut filter, and adjusts the amount or wavelength of light to be detected.

The epi-illumination light source unit 24 and the transmission light source unit 26 respectively have, for example, an excitation light source and a white light source for fluorescence imaging, and are configured to switch the light sources under the control of the imaging control device 100 as necessary. For example, when performing imaging to detect fluorescence emitted from the fluorescence-labeled object S, the object S is irradiated with excitation light from the epi-illumination light source unit 24 or the transmission light source unit 26, when performing imaging to detect reflected light from the object S, the object S is irradiated with white light from the epi-illumination light source unit 24, and when performing imaging to detect transmission light transmitted through the object 5, the object S is irradiated with white light from the transmission light source unit 26.

The object observation monitor 50 displays a state on the stage 6 which is imaged by a small camera (not shown) provided in the upper portion of the housing 12. With this, it is possible to confirm the position of the object S placed on the stage 16 or the height of the stage 16, and to adjust the position of the object or the height of the stage such that the object S is placed suitably for imaging.

The imaging device body 10 of this embodiment has the configuration described above, and can perform imaging by four imaging methods according to the type of object or the purpose of imaging. The four imaging methods include an imaging method (hereinafter, referred to as a first imaging method) which detects chemiluminescence emitted from the object, an imaging method (hereinafter, referred to as a second imaging method) which detects fluorescence emitted from the object, an imaging method (hereinafter, referred to as a third imaging method) which detects reflected light reflected from the object, and an imaging method (hereinafter, referred to as a fourth imaging method) which detects transmission light transmitted through the object.

In the first imaging method, when an object molecule excited by a chemical reaction returns to a ground state, a phenomenon (chemiluminescence) of energy being discharged as light is used. With this, for example, genetic analysis, inspection and research of biological tissues relating to diseases and aging, deterioration evaluation of organic compounds and polymer compounds, and the like can be performed. For example, a substance to be imaged in the object is labeled by a labeling substance which generates chemiluminescence if coming into contact with a chemiluminescent substance, and thereafter, the chemiluminescent substance is brought into contact with the labeling substance, whereby chemiluminescence can be generated. In the first imaging method, light irradiation from the epi-illumination light source unit 24 and the transmission light source unit 26 is not performed.

In the second imaging method, excitation light from the epi-illumination light source unit 24 or the transmission light source unit 26 is irradiated, and fluorescence from a fluorescent substance labeling a substance to be imaged in the object is detected. As an object for the second imaging method, for example, a gel support including a DNA (deoxyribonucleic acid) segment fluorescence-labeled and separated by electrophoresis is given. If the imaging device 1 of this embodiment is used, the distribution of the DNA segment in the gel support can be imaged and analyzed.

In the third imaging method, for example, white light is irradiated from the epi-illumination light source unit 24 as illumination light, and reflected light of illumination light by the object is detected. With this, a digital image can be obtained by photoelectrically reading a reflective original, such as a photograph. In the fourth imaging method, for example, white light is irradiated from the transmission light source unit 26 as illumination light, and transmission light of illumination light transmitted through the object is detected. With this, a digital image can be obtained by photoelectrically reading a transmissive original, such as a film.

The imaging control device 100 is constituted of, for example, a personal computer, and includes a control device body 102, an input unit 104, and a display unit 106.

The imaging control device 100 controls the operations of the imaging unit 20, the epi-illumination light source unit 24, and the transmission light source unit 26 of the imaging, device body 10 to control the imaging function of the object S described above. The imaging control device 100 has an analysis function of analyzing an image captured by the imaging unit 20 and a file operation function of a file including an image captured by the imaging unit 20. The analysis function and the file operation function will be described, below in detail.

As shown in FIG. 4, the control device body 102 includes an image processing unit 108, an image analysis unit 110, a file operation unit 112, a terminal recognition unit 114, and a control unit 116.

The image processing unit 108 receives an image signal output from the imaging unit 20 as input, and subjects the image signal to, for example, signal processing, such as noise elimination processing or sharpness processing.

The image analysis unit 110 executes the analysis function described above, and analyzes an image of chemiluminescence captured by the first imaging method or an image of fluorescence captured by the second imaging method.

Specifically, the image analysis unit 110 acquires, for example, an image obtained by imaging chemiluminescence or fluorescence of DNA separated by electrophoresis, RNA (ribonucleic acid), or protein, acquires feature quantities, such as the position of a band in the image, the concentration of the band, and the size of the band, and analyzes the feature quantities. In the case of protein, the molecular weight of protein can be determined by the position of the band, and the expression amount of protein can be determined by the concentration and site of the band. A method of image analysis is not limited thereto, and other known methods can be used.

The file operation unit 112 executes the file operation function described above, stores a file including an image captured by the imaging unit 20, and performs a file operation of the stored file.

Information of the file stored in the file operation unit 112 is output to the first to third external terminals 2 to 4 shown in FIG. 1, and the first to third external terminals 2 to 4 display the input information of the file. The first to third external terminals 2 to 4 receive an instruction input of a file operation from the user, and each file stored in the file operation unit 112 is subjected to a file operation based on control information output from the first to third external terminals 2 to 4. Examples of the file operation include file copy, move, delete, rename, and the like, and may include other known file operations.

The terminal recognition unit 114 recognizes the first to third external terminals 2 to 4 shown in FIG. 1 individually. Specifically, the terminal recognition unit 114 has a wireless communication function, acquires identification information of each external terminal output from each of the external terminals 2 to 4 through wireless communication, and recognizes the first to third external terminals 2 to 4 individually based on the identification information. As the identification information, a media access control address (MAC address) may be used. Each external terminal may be recognized using a dedicated password or the like. The terminal recognition unit 114 receives control information output from the first to third external terminals 2 to 4 through wireless communication and outputs the control information to the control unit 116.

The control unit 116 includes, for example, a central processing unit (CPU), a read only memory (ROM), and the like. The control unit 116 integrally controls the operations of the imaging device body 10 and the imaging control device 100. In this embodiment, the control unit 110 corresponds to a control unit of the invention.

In particular, the control unit 116 of this embodiment receives the control information output from the first to third external terminals 2 to 4, and controls the imaging function of the imaging device body 10 and the image analysis function and the file operation function of the imaging control device 100 based on the received control information.

Specifically, the control unit 116 of this embodiment recognizes the execution state of the above-described imaging function, the analysis function, and the file operation function by each external terminal based on the recognition information of each external terminal recognized by the terminal recognition unit 114 and the received control information in real time. Then, the control unit 116 restricts simultaneous processing of the imaging, function by a plurality of external terminals based on the execution state of each function of each external terminal and enables the execution of parallel processing of the imaging function by one external terminal of the first to third external terminals 2 to 4 and the image analysis function and the file operation function by other external terminals. The control of the imaging, function, the image analysis function, and the file operation function by each external terminal will be described below in detail.

The display unit 106 includes, for example, a display device, such as a cathode ray tube (CRT) display or a liquid crystal display, and displays an image captured by the imaging unit 20, or the like. Similarly to the first to third external terminals 2 to 4, the display unit 106 displays file information stored in the file operation unit 112.

The input unit 104 includes input devices, such as a mouse and a keyboard. The user performs various settings of the respective units of the imaging device body 10 and the imaging control device 100 using the input unit 104. Similarly to the first to third external terminals 2 to 4, the input unit 104 receives operation instruction inputs of the imaging function of the imaging device body 10, the image analysis function and the file operation function of the imaging control device 100, and the like.

Next, the first to third external terminals 2 to 4 will be described in detail. The first to third external terminals 2 to 4 are constituted of, for example, tablet terminals. The first to third external terminals 2 to 4 receive an operation instruction input of the imaging device 1 from the user and output the control information to the imaging device 1 based on the received operation instruction input.

Figure 5:
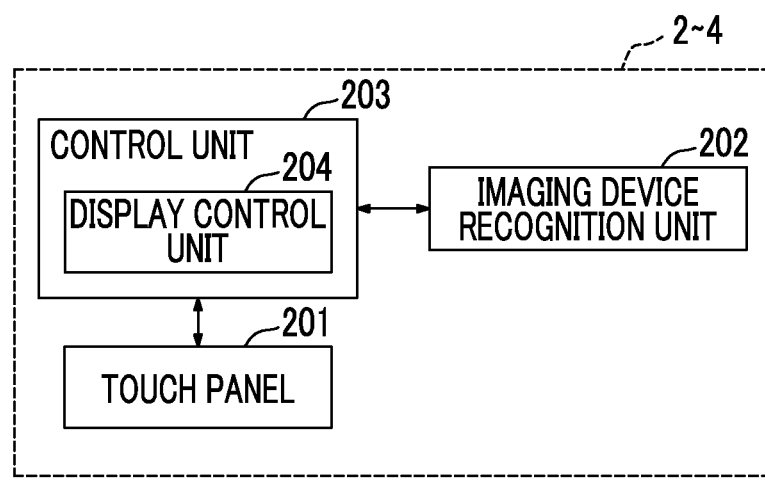
FIG. 5 is a block diagram showing the schematic configuration of first to third external terminals.

FIG. 5 is a block diagram showing the schematic configuration of the first to third external terminals 2 to 4. As shown in FIG. 5, the first to third external terminals 2 to 4 respectively include a touch panel 201 an imaging device recognition unit 202, and a control unit 203.

The touch panel 201 displays an operation instruction input screen on which an operation instruction input of the imaging device 1 from the user is received, and receives an instruction input of the above-described imaging function, the analysis function, and the file operation function on the operation instruction input screen. The operation instruction input screen will be described below in detail.

The imaging device recognition unit 202 recognizes the imaging device 1 and outputs control information according to the operation instruction input from the user to the imaging device 1. Specifically, the imaging device recognition unit 202 has a wireless communication function, recognizes the imaging device 1 through wireless communication, and outputs the control information. The imaging device recognition unit 202 acquires information of the execution state of the imaging function, the analysis function, and the file operation function in the imaging device 1.

The control unit 203 integrally controls the operation of the external terminal. The control unit 203 outputs the control information according to the operation instruction input from the user to the imaging device recognition unit 202.

The control unit 203 includes a display control unit 204, and the display control unit 204 displays the operation instruction input screen described above on the touch panel 201. The display control unit 204 displays the execution states of the functions of the imaging device 1 acquired by the imaging device recognition unit 202 on the touch panel 201 in real time. The display control by the display control unit 204 will be described below in detail.

In this embodiment, although tablet terminals are used as the first to third external terminals 2 to 4, the invention is not limited thereto, and a personal computer connected through a wireless communication line or a wired communication line, such as a local area network (LAN), may be used.

The network server 5 is a data server which is designated as a movement destination of a file stored in the file operation unit 112 of the imaging device 1, and is connected to the imaging device 1 through a wireless communication line or a wired communication line. The storage device 6 is also a storage medium which is designated as a movement destination of a file stored in the file operation unit 112 of the imaging device 1, and is constituted of, for example, a universal serial bus (USB) memory, a USB hard disk, or the like.

Next, the action of the imaging system of this embodiment will be described referring to the drawings. The imaging system of this embodiment has a feature of a control method of each function of the imaging device 1 by the first to third external terminals 2 to 4, and description will be provided focusing on this feature.

Figure 6:
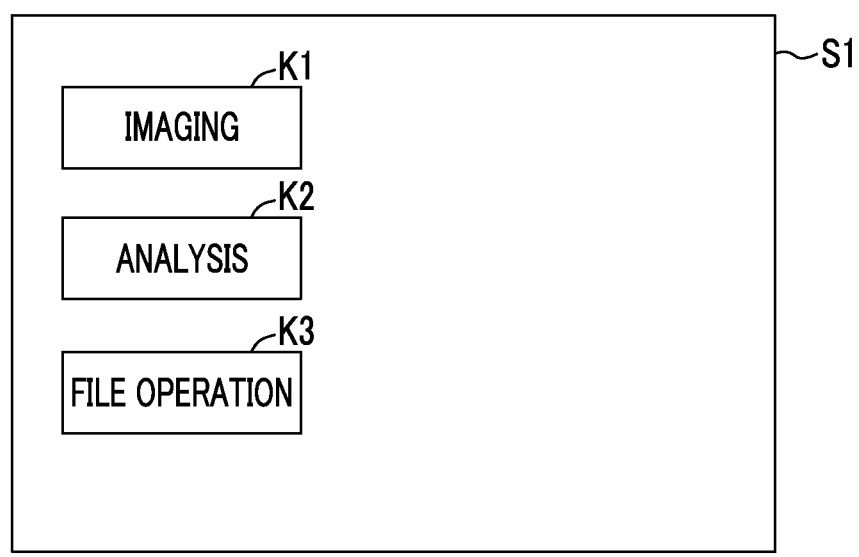
FIG. 6 is a diagram showing an example of an operation instruction input screen of an external terminal when the imaging device is not controlled by the external terminal.

First, when all of the external terminals do not control the imaging device 1, an operation instruction input screen S1 shown in FIG. 6 is displayed on the touch panel 201 of each of the first to third external terminals 2 to 4. Specifically, an "IMAGING" key which receives an instruction to execute the imaging function, an "ANALYSIS" key K2 which receives an instruction to execute the analysis function, and a "FILE OPERATION" key K3 which receives an instruction to execute the file operation are displayed on the operation instruction input screen S1.

For example, if the "IMAGING" key K1 is depressed by a first user on the touch panel 201 of the first external terminal 2, the control unit 203 of the first external terminal 2 generates control information for controlling the imaging function. The control information for controlling the imaging function and the identification information of the first external terminal 2 are output from the imaging device recognition unit 202 of the first external terminal 2 to the imaging device 1.

Figure 7:
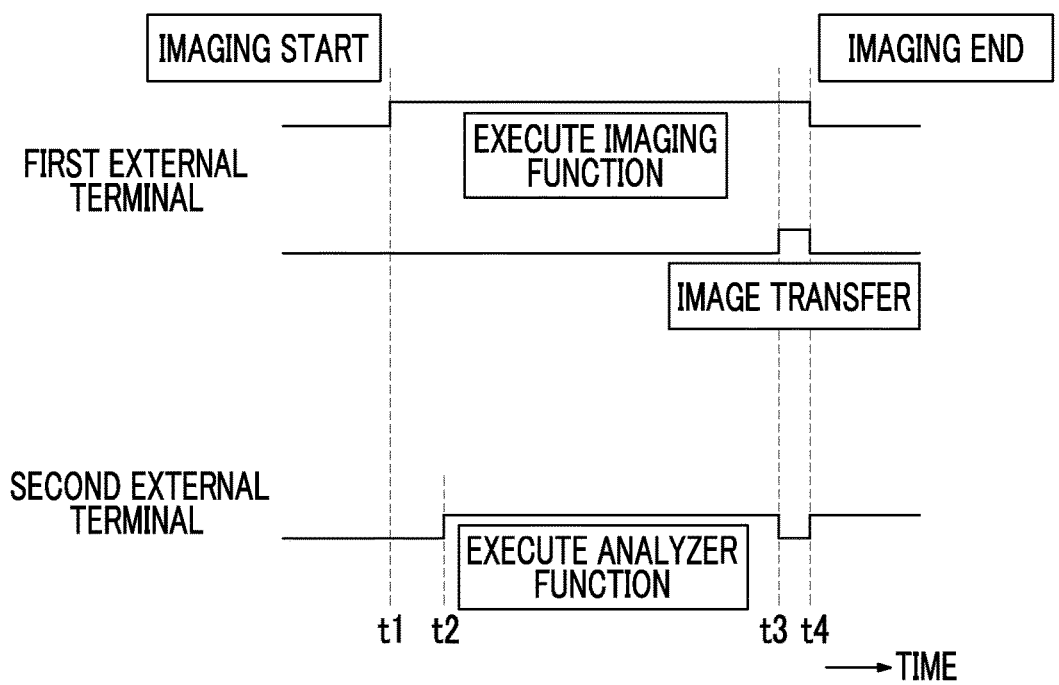
FIG. 7 is a timing chart illustrating a case where an analysis function is executed by the second external terminal while an imaging function is being executed by the first external terminal.

If the control information of the imaging function output from the first external terminal 2 is received, the imaging device 1 executes the imaging function. FIG. 7 is a timing chart showing the control timing of the imaging function by the first external terminal 2 and the control timing of the analysis function by the second external terminal 3. As shown m FIG. 7, the imaging function is executed from the time t1 in the imaging device 1 based on the control information output from the first external terminal 2.

If the imaging function of the imaging device 1 is executed, the control unit 116 of the imaging device 1 recognizes the imaging function being executed based on the control information output from the first external terminal 2, and outputs the execution information to the second external terminal 3 and the third external terminal 4.

Figure 8:
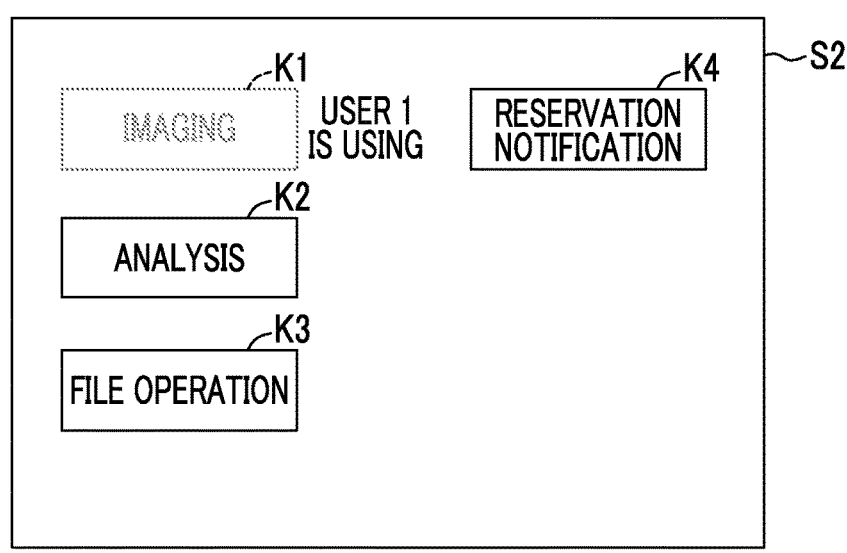
FIG. 8 is a diagram showing an example of the operation instruction input screen of each of the second and third external terminals when the first external terminal executes the imaging function of the imaging device.

The second external terminal 3 and the third external terminal 4 receive the execution information of the imaging function output from the imaging device 1 by the imaging device recognition unit 202, and change the content of the operation instruction input screen displayed on the touch panel 201 according to the execution information. Specifically, as shown in FIG. 8, on an operation instruction input screen S2 of each of the second external terminal 3 and the third external terminal 4, the "IMAGING" key K1 is grayed out, and the reception of the operation instruction input of the imaging function from a second user and a third user is prohibited. With this, the execution of the imaging function of the imaging device 1 is restricted to only the first external terminal 2. That is, the operation instruction input screen in the second external terminal 3 and the third external terminal 4 is changed based on the execution information output from the control unit 116 of the imaging device 1, and accordingly, the execution of the imaging function of the imaging device 1 is restricted to only the first external terminal 2.

On the operation instruction input screen S2 of each of the second external terminal 3 and the third external terminal 4, as shown in FIG. 8, a message of "USER 1 IS USING" indicating that the first user is executing the imaging function using the first external terminal 2 is displayed on the right side of the "IMAGING" key K1. On the operation instruction input screen S2 of each of the second external terminal 3 and the third external terminal 4, a "RESERVATION NOTIFICATION" key K4 for reserving the execution of the imaging function is displayed on the right side of the "IMAGING" key K1.

The "RESERVATION NOTIFICATION" key K4 is a key which receives the reservation of execution of the imaging function of the imaging device 1. If the "RESERVATION NOTIFICATION" key K4 is depressed by the second or third user, imaging function reservation information is output from the control unit 203 of the second or third external terminal 3 or 4, and is output to the imaging device 1 through the imaging device recognition unit 202.

The imaging device 1 receives the imaging function reservation information by the terminal recognition unit 114, and the control unit 116 of the imaging device 1 performs control such that the imaging function is executed by each external terminal in the order of reception of the imaging function reservation information.

While the imaging function is being executed by the first external terminal 2, as described above, in the second external terminal 3 and the third external terminal 4, the operation instruction input of the imaging function is not received; however, as shown in FIG. 8, the "ANALYSIS" key K2 and the "FILE OPERATION" key K3 remain unchanged, and the operation instruction inputs of the analysis function and the file operation function are enabled. That is, while the imaging function is being executed by the first external terminal 2, the analysis function or the file operation function by the second external terminal 3 or the third external terminal 4 can be executed in parallel. It is assumed that the same function cannot be executed by the second external terminal 3 and the third external terminal 4. That is, each of the first to third external terminals 2 to 4 can execute only a function which is not executed by other external terminals.

For example, while the imaging function is being executed by the first external terminal 2, if the "ANALYSIS" key K2 is depressed by the second user on the operation instruction input screen S2 of the second external terminal 3, the control unit 203 of the second external terminal 3 generates control information for controlling the analysis function. The control information for controlling the analysis function and the identification information of the second external terminal 3 are output from the imaging device recognition unit 202 of the second external terminal 3 to the imaging device 1.

If the control information of the analysis function output from the second external terminal 3 is received, as shown in the timing chart of FIG. 7, the imaging device executes the analysis function by the second external terminal 3 from the time t2 in parallel with the imaging function by the first external terminal 2. An image to be analyzed at this time may be an image which is captured by the second user and stored in the file operation unit 112, or may be an image selected by a file operation function described below. When performing the analysis function, an image to be analyzed may be transmitted from the second external terminal 3 to the imaging device 1.

As described above, when the imaging function by the first external terminal 2 and the analysis function by the second external terminal. 3 are executed in parallel, and as shown in the timing chart of FIG. 7, when transferring art image captured by the imaging function by the first external terminal 2 from the imaging device 1 to the first external terminal 2, it is desirable that, during the period of the image transfer, the execution of the analysis function by the second external terminal 3 is interrupted. That is, it is desirable that, during a period from the time t3 to the time t4 shown in FIG. 7, the execution of the analysis function by the second external terminal 3 is interrupted. This is because the image transfer and the analysis function use the CPU of the control unit 116 together; however, if these functions are processed in parallel, the time of the image transfer is extremely extended, and the execution of the imaging function by the external terminals other than the first external terminal 2 is delayed. In this embodiment, although the above-described image transfer processing is included in the imaging function, the image transfer processing may not necessarily be included in the imaging function.

As described above, if the analysis function is executed by the second external terminal 3, the control unit 116 of the imaging device 1 outputs the execution information to the first external terminal 2 and the third external terminal 4.

Figure 9:
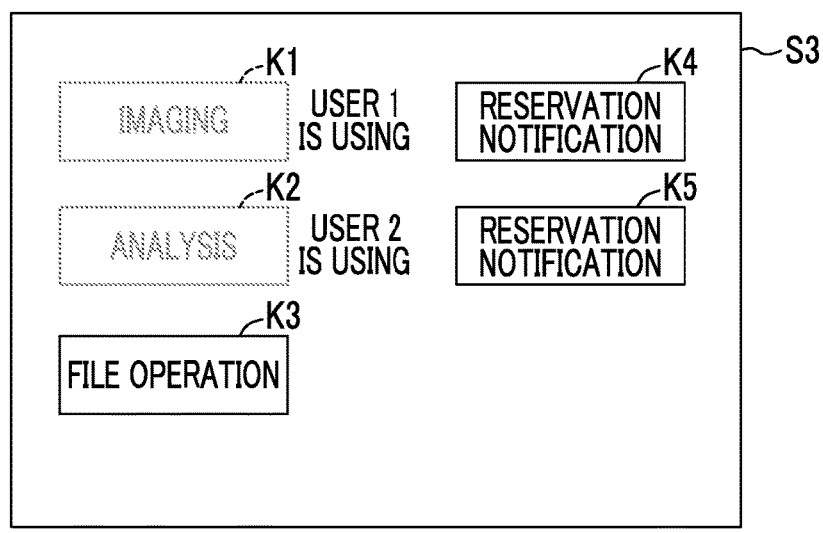
FIG. 9 is a diagram showing an example of the operation instruction input screen of the third external terminal when the first external terminal executes the imaging function of the imaging device and the second external terminal executes the analysis function of the imaging device.

The first external terminal 2 and the third external terminal 4 receive execution information of the analysis function by the second external terminal 3 by the imaging device recognition unit 202, and change the content of the operation instruction input screen according to the execution information. Specifically, for example, in the third external terminal 4, as shown in FIG. 9, the "ANALYSIS" key K2 is grayed out along with the "IMAGING" key K1 of an operation instruction input screen S3, and the reception of the analysis function of the operation instruction input from the third user is prohibited. With this, the execution of the analysis function of the imaging device 1 is restricted to only the second external terminal 3. The "ANALYSIS" key K2 of the operation instruction input screen of the first external terminal 2 is grayed out. That is, based on the execution information output from the control unit 116 of the imaging device 1, the operation instruction input screen in the first external terminal 2 and the third external terminal 4 is changed, and accordingly, the execution of the analysis function of the imaging device 1 is restricted to only the second external terminal 3.

On the operation instruction input screen S3 of the third external terminal 4, as shown in FIG. 9, a message of "USER 2 IS USING" indicating the second user is executing the analysis function using the second external terminal 3 is additionally displayed on the right side of the "ANALYSIS" key K2. On the operation instruction input screen S3 of the third external terminal 4, a "RESERVATION NOTIFICATION" key K5 for reserving the execution of the analysis function of the imaging device 1 is additionally displayed on the right side of the "ANALYSIS" key K2. On the operation instruction input screen of the first external terminal 2, the message of "USER 2 IS USING" and the "RESERVATION NOTIFICATION" key K5 are displayed on the right, side of the "ANALYSIS" key K2.

The "RESERVATION NOTIFICATION" key K5 is a key which receives the reservation of execution of the analysis function of the imaging device 1. If the "RESERVATION NOTIFICATION" key K5 is depressed by the first or third user, analysis function reservation information is output from the control unit 203 of the first or third external terminal 2 or 4, and is output to the imaging device 1 by the imaging device recognition unit 202.

The imaging device 1 receives the analysis function reservation information by the terminal recognition unit 114, and the control unit 116 of the imaging device 1 performs control such that the analysis function is executed by each external terminal in the order of reception of the analysis function reservation information.

As described above, while the imaging function is being executed by the first external terminal 2 and the analysis function is being executed by the second external terminal 3, the operation instruction inputs of the imaging function and the analysis function are not received by the third external terminal 4; however, as shown in FIG. 9, the "FILE OPERATION" key K3 remains unchanged, and the operation instruction input of the file operation function is enabled. That is, while the imaging function is being executed by the first external terminal 2 and the analysis function is being executed by the second external terminal 3, the file operation function can be executed by the third external terminal 4 in parallel.

If the "FILE OPERATION" key K3 is depressed by the third user on the operation instruction input screen S3 of the third external terminal 4, the control unit 203 of the third external terminal 4 generates control information for controlling the file operation function. The control information for controlling the file operation function and the identification information of the third external terminal 4 are output from the imaging device recognition unit 202 to the imaging device 1.

If the control information of the analysis function output from the third external terminal 4 is received, the imaging device 1 executes the file operation function by the third external terminal 4 in parallel with the imaging function by the first external terminal 2 and the analysis function by the second external terminal 3. Hereinafter, the file operation function will be described.

If the file operation function is executed, the control unit 116 of the imaging device 1 acquires information of a file name stored in the file operation unit 112 and outputs information of the file name to the third external terminal 4.

Figure 10:
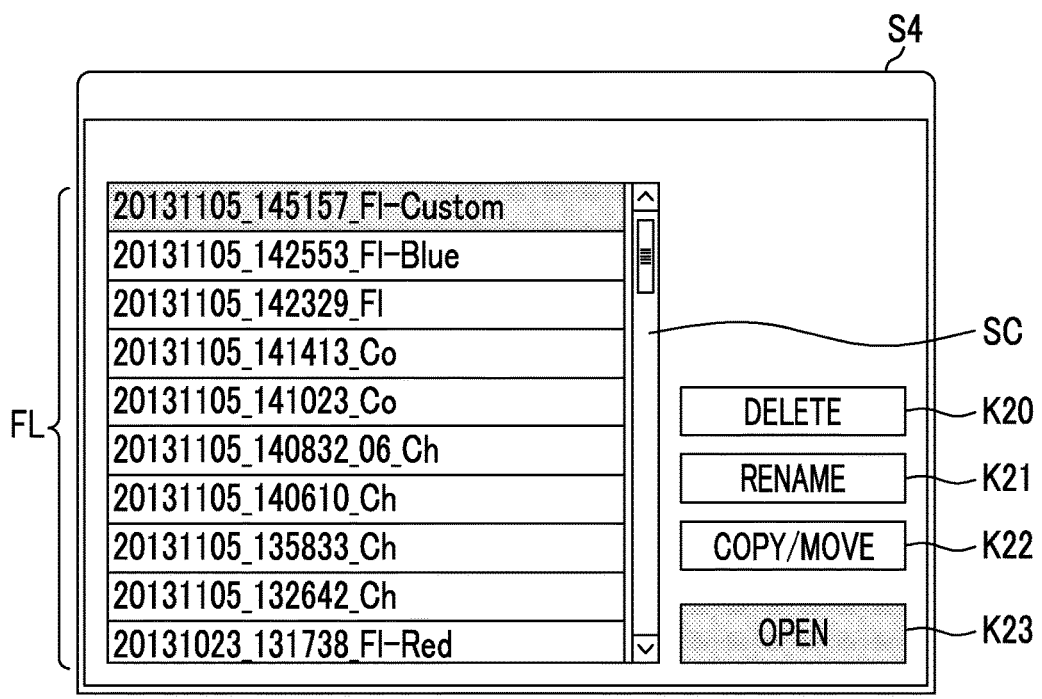
FIG. 10 is a diagram showing a file operation screen.

The third external terminal 4 receives information of the file name output from the imaging device 1 by the imaging device recognition unit 202, and the display control unit 204 of the third external terminal 4 displays a file operation screen S4 shown in FIG. 10 on the touch panel 201 based on the received information of the file name. On the file operation screen S4, as shown in FIG. 10, a file name display column FL in which file names are listed and displayed, a "DELETE" key K20 which receives an input of an instruction to delete a file, a "RENAME" key K21 which receives an input of an instruction to change a file name, a "COPY/MOVE" key K22 which receives an input of an instruction to move and copy a file, and an "OPEN" key K23 which receives an input of an instruction to open a file are displayed.

For example, in the file name display column FL, a predetermined file name is selected by the third user, and a file operation is performed for the selected file. For example, when the "DELETE" key K20 is depressed by the third user, the selected file name and deletion information are output from the imaging device recognition unit 202 of the third external terminal 4 to the imaging device 1. The file operation unit 112 of the imaging device 1 deletes the selected file according to the input information.

When the "RENAME" key K21 is depressed by the third user, an input screen of a new file name is displayed on the touch panel 201 of the third external terminal 4, and an input of the new file name from the third user is received. The new file name input on the input screen is output from the imaging device recognition unit 202 of the third external terminal 4 to the imaging device 1. The file operation unit 112 of the imaging device 1 changes the file name of the selected file based on the input new file name.

When the "COPY/MOVE" key K22 is depressed by the third user, a movement destination designation screen on which a movement destination of a copied file is designated is displayed on the touch panel 201 of the third external terminal 4, and the designation of the movement destination by the third user is received. The movement destination of the copied file is, for example, a predetermined drive or folder in the third external terminal 4, a predetermined drive or a folder in the network server 5 and the storage device 6 connected to the imaging device 1, or the like.

If the movement destination of the copied file is designated on the movement destination designation screen by the third user, the selected file name and the information of the movement destination are output from the imaging, device recognition unit 202 of the third external terminal 4 to the imaging device 1. The file operation unit 112 of the imaging device 1 reads the selected file to create a copy and transfers the copied file to the designated movement, destination according to the input information.

When the "OPEN" key K23 is depressed by the third user, the selected file name is output from the imaging device recognition unit 202 of the third external terminal 4 to the imaging device 1. The file operation unit 112 of the imaging device 1 reads the selected file to create a copy and transfers the copied file to the third external terminal 4 according to the input information. The control unit 203 of the third external terminal 4 opens the transferred file to display an image on the touch panel 201. When a file already transferred to the third external terminal 4 is selected, the above-described transfer is not performed, and the selected file is opened.

As described above, if the file operation function is executed by the third external terminal 4, the control unit 116 of the imaging device 1 outputs information of the execution state to the first external terminal 2 and the second external terminal 3.

The first external terminal 2 and the second external terminal 3 receive the execution information of the file operation function by the third external terminal 4 by the imaging device recognition unit 202, and change the content of the operation instruction input screen according to the execution information. Specifically, the "FILE OPERATION" key K3 of the operation instruction input screen is grayed out, and the reception of the operation instruction input of the file operation function from the first user and the second user is prohibited. With this, the execution of the file operation function of the imaging device 1 is restricted to only the third external terminal 4.

On the operation instruction input screen of each of the first external terminal 2 and the second external terminal 3, a message of "USER 3 IS USING" indicating that the third user is executing the file operation function using the third external terminal 4 is additionally displayed on the right side of the "FILE OPERATION" key K3.

According to the imaging system of the embodiment described above, the control unit 116 of the imaging device 1 recognizes the execution states of the functions by each external terminal based on the control information output from each external terminal, restricts simultaneous processing of the imaging function by a plurality of external terminals and simultaneous processing of the analysis function and simultaneous processing of the file operation function, and performs parallel processing of the imaging function, the analysis function, and the file operation function by a plurality of external terminals; therefore, it is possible to allow efficient use of the imaging device 1 by multiple users and to achieve improvement of the rate of operation.

Figure 11:
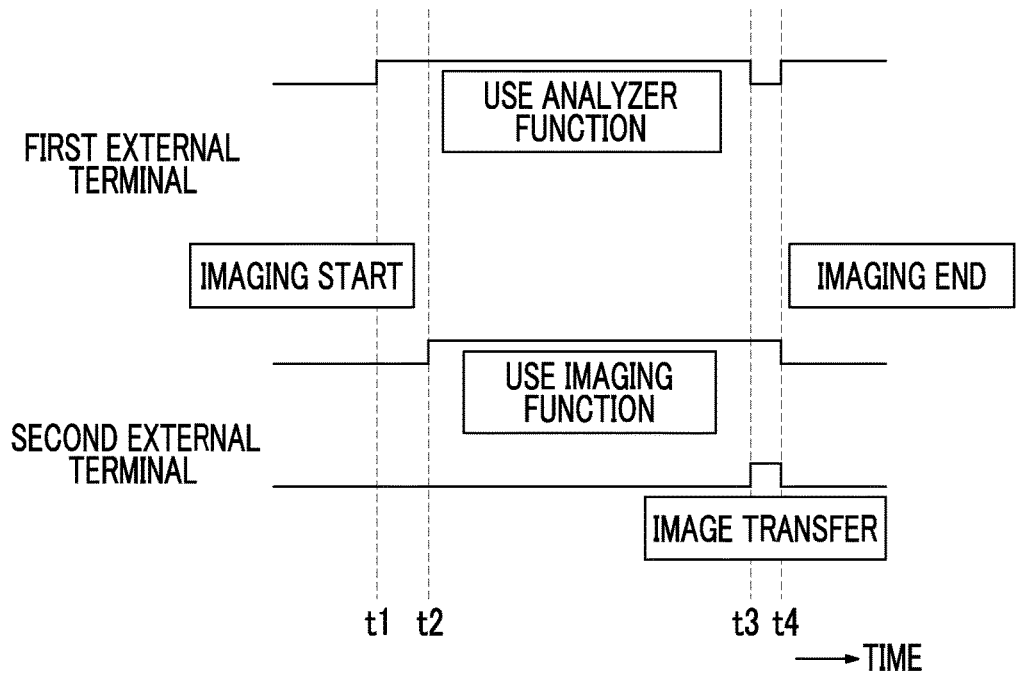
FIG. 11 is a timing chart illustrating a case where the imaging function is executed by the second external terminal while the analysis function is being executed by the first external terminal.

In the above description, although a case where the analysis function is executed by the second external terminal 3 in parallel while the imaging function is being executed by the first external terminal 2 has been described referring to the timing chart of FIG. 7, a timing chart of FIG. 11 shows a case where the imaging function is executed by the second external terminal 3 in parallel while the analysis function is being executed by the first external terminal 2. Hereinafter, the timing chart of FIG. 11 will be described.

As shown in the timing chart of FIG. 11, if the analysis function of the imaging device 1 is executed by the first external terminal 2, the control unit 116 of the imaging device 1 outputs the execution information to the second external terminal 3 and the third external terminal 4.

Figure 12:
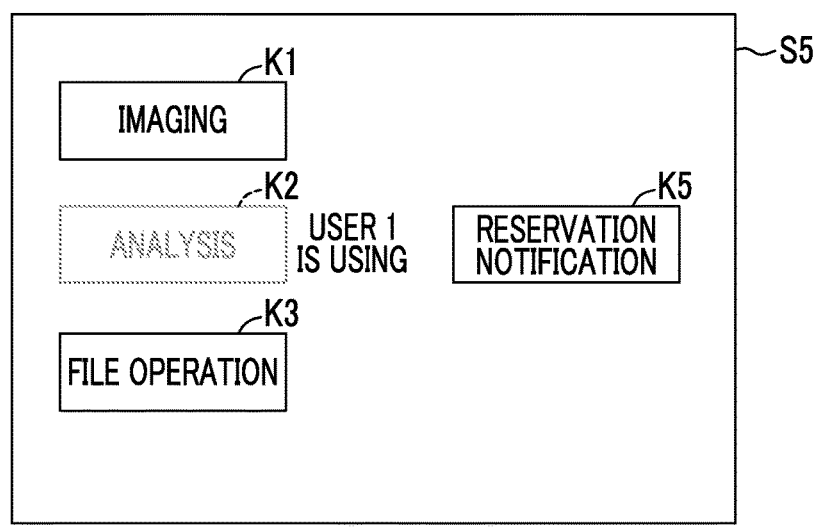
FIG. 12 is a diagram showing an example of the operation instruction input screen of each of the second and third external terminals when the first external terminal executes the analysis function of the imaging device.

The second external terminal 3 and the third external terminal 4 receive the execution information of the analysis function by the first external terminal 2 by the imaging device recognition unit 202, and change the content of the operation instruction input screen according to the execution information. Specifically, as shown in FIG. 12, the "ANALYSIS" key K2 of the operation instruction input screen S4 of each of the second external terminal 3 and the third external terminal 4 is grayed out, and the reception of the operation instruction input, of the analysis function from the second user and the third user is prohibited. With this, the execution of the analysis function of the imaging device 1 is restricted to only the first external terminal 2.

On an operation instruction input screen S5 of each of the second external terminal 3 and the third external terminal 4, as shown in FIG. 12, a message of "USER 1 IS USING" indicating that the first user is executing the analysis function using the first external terminal 2 is displayed on the right side of the "ANALYSIS" key K2. On the operation instruction input screen S5 of each of the second external terminal 3 and the third external terminal 4, the "RESERVATION NOTIFICATION" key K5 for reserving the execution of the analysis function of the imaging device 1 is displayed on the right side of the "ANALYSIS" key K2.

If the "RESERVATION NOTIFICATION" key K5 is depressed by the second or third user, the analysis function reservation information is output from the control unit 203 of the second or third external terminal 3 or 4, and is output to the imaging, device 1 by the imaging device recognition unit 202.

The imaging device 1 receives the analysis function reservation information by the terminal recognition unit 114, and the control unit 116 of the imaging device 1 performs control such that the analysis function is executed by each external terminal in the order of reception of the analysis function reservation information.

While the analysis function is being executed by the first external terminal 2, as described above, the operation instruction input of the analysis function is not received by the second external terminal 3 and the third external terminal 4; however, as shown in FIG. 12, the "IMAGING" key K1 and the "FILE OPERATION" key K3 remain unchanged, and the operation instruction inputs of the imaging function and the file operation function are enabled. That is, while the imaging function is being executed by the first external terminal 2, the imaging function or the file operation function can be executed by the second external terminal 3 in parallel.

For example, if the "IMAGING" key K1 is depressed by the second user on the touch panel 201 of the second external terminal 3, the control unit 203 of the second external terminal 3 generates control information for controlling the imaging function. The control information for controlling the imaging function and the identification information of the second external terminal 3 are output from the imaging device recognition unit 202 to the imaging device 1.

If the control information of the imaging function output from the second external terminal 3 is received, the imaging device 1 executes the imaging function.

The analysis function by the first external terminal 2 and the imaging function by the second external terminal 3 are executed in parallel; however, in this case, as shown in the timing chart of FIG. 11, when transferring an image captured by the imaging function by the second external terminal 3 from the imaging device 1 to the second external terminal 3, it is desirable that, daring the period of the image transfer, the execution of the analysis function by the first external terminal 2 is interrupted. That is, it is desirable that, during the period from the time t3 to the time t4 shown in FIG. 11, the execution of the analysis function by the first external terminal 2 is interrupted.

In the above description, although the imaging function is executable by the second external terminal 3 while the analysis function is being executed by the first external terminal 2, at this time, when a permission is obtained by the first user, the imaging function may be executable.

Specifically, for example, when the "IMAGING" key K1 of the second external terminal 3 is depressed by the second user, the control unit 116 of the imaging device 1 outputs a control signal notifying the effect to the first external terminal 2 before executing the imaging function. The display control unit 204 of the first external terminal 2 displays an "IMAGING PERMISSION" key and an "IMAGING PROHIBITION" key on the touch panel 201 according to the input control signal. When the "IMAGING PERMISSION" key is depressed by the first user, the control unit 116 of the imaging device 1 executes the imaging function. When the "IMAGING PROHIBITION" key is depressed by the first user, the control unit 116 of the imaging device 1 outputs a signal notifying the effect to the second external terminal 3, and displays a message to the effect of imaging being not permitted on the touch panel 201 of the second external terminal 3.

Figure 13:
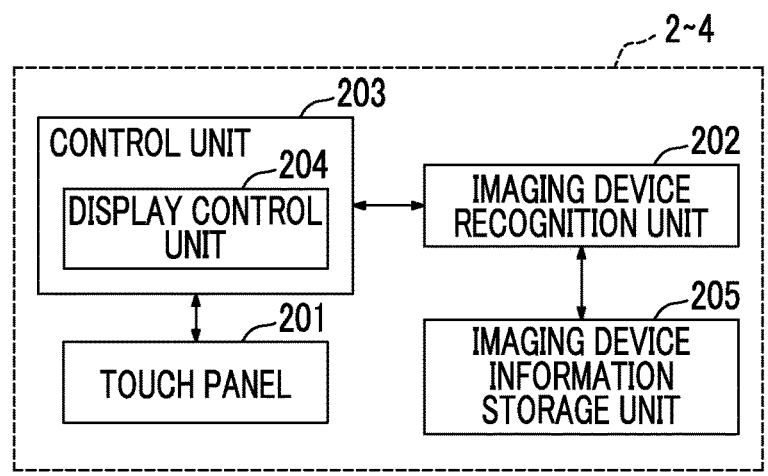
FIG. 13 is a block diagram showing another embodiment of the first to third external terminals.

In the description of the embodiment described above, although a case where the functions of one imaging device 1 are controlled by a plurality of external terminals has been described, the number of imaging devices 1 may not necessarily be one, and the functions of a plurality of imaging devices may be controlled by a plurality of external terminals. In this case, for example, as shown in FIG. 13, in each external terminal, an imaging device information storage unit 205 which stores registration information of the plurality of imaging devices may be provided, and an imaging device recognition unit 202 may recognize a plurality of imaging devices based on the registration information. The control of the functions of each imaging device by a plurality of external terminals is the same as in the embodiment described above.

Figure 14:
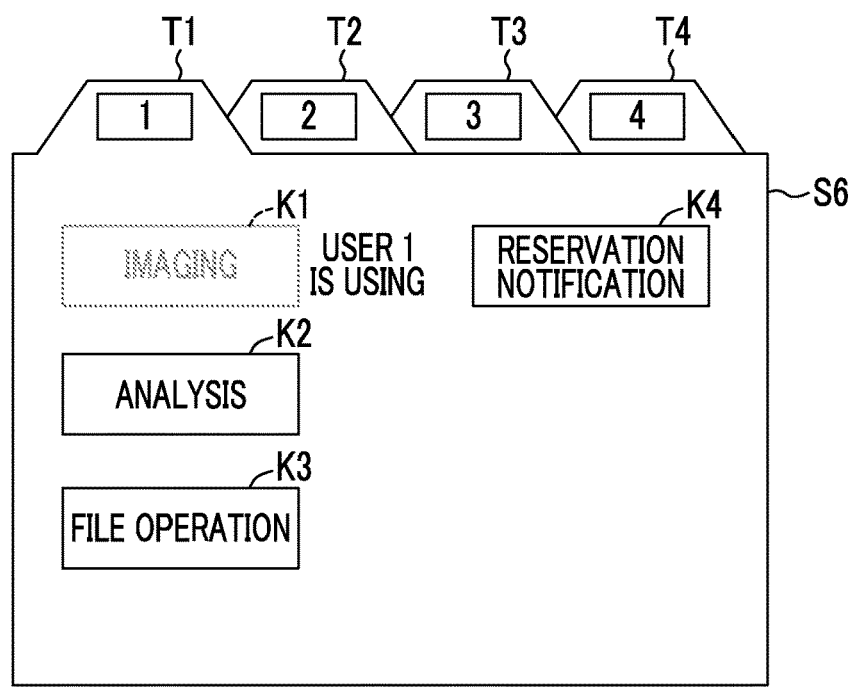
FIG. 14 is a diagram showing an example of an operation instruction input screen which is displayed on an external terminal when there are a plurality of imaging devices.

FIG. 14 shows an example of an operation instruction input screen S6 which is displayed on each external terminal when there are a plurality of imaging devices. The operation instruction input screen S6 shown in FIG. 14 is an example when there are our imaging devices, and four tags T1 to T4 for receiving operation instruction inputs of respective functions of respective imaging devices are displayed.

FIG. 14 shows an operation instruction input screen when the tag T1 is selected, and on the operation instruction input screen, an operation instruction input of each function of a first imaging device is received. When the tag T2 is selected, the operation instruction input screen is changed, and an operation instruction input of each function of a second imaging device is received. In this way, the user can select an imaging device to be controlled by selecting the tags T1 to T4.

Figure 15:
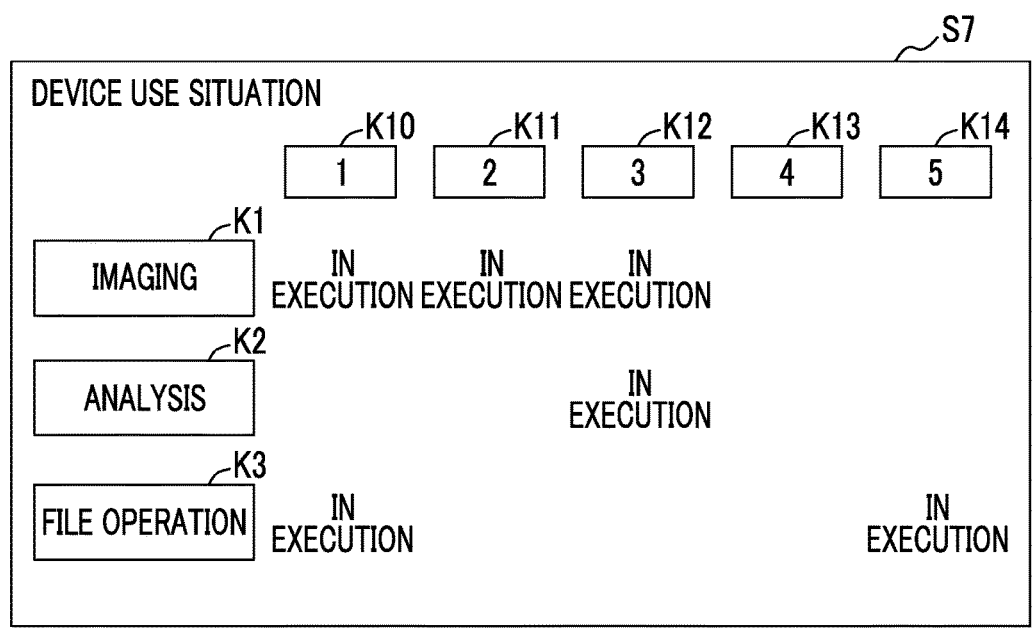
FIG. 15 is a diagram showing an example of list display of imaging devices which is displayed on an external terminal when there are a plurality of imaging devices.

When there are a plurality of imaging devices, execution information of each function in each external terminal may be listed and displayed in each imaging device. FIG. 15 shows an example of a list display screen S7 when there are five imaging devices. On the list display screen S7, imaging device selection keys K10 to K14 are displayed, and execution information of each function of each imaging device is displayed below each key. For example, execution information indicating that the imaging function and the file operation function are being executed in the first imaging device is displayed below the imaging device selection key K10, and execution information indicating that only the imaging function is being executed in the second imaging device is displayed below the imaging device selection key K11. For example, when each of the imaging device selection keys K10 to K14 is depressed by the user, an operation instruction input screen of an imaging device corresponding to the imaging device selection key is displayed, execution information of the imaging device is displayed, and an operation instruction input from the user is enabled. As a plurality of imaging devices, imaging devices of different types may be used.

Figure 16:
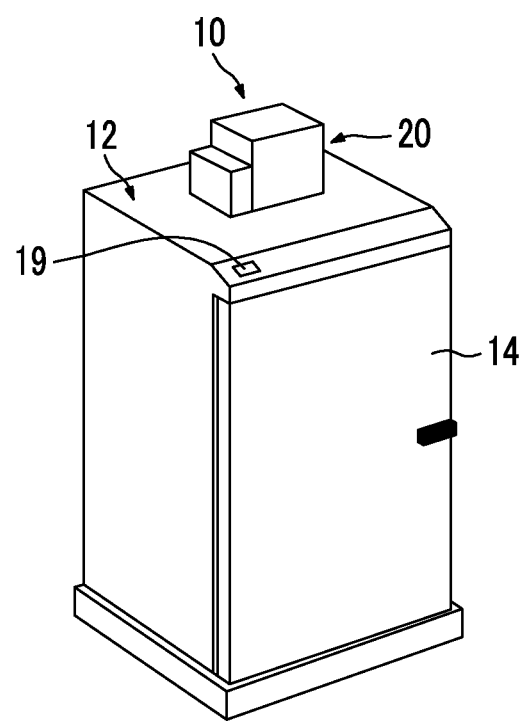
FIG. 16 is a schematic perspective view showing an example of an imaging device which is provided with a light emitting unit.

As described above, when there are a plurality of imaging devices, the user may want to specify an imaging device whose operation is actually instructed using, an external terminal. In this case, for example, a "CONNECTION CONFIRMATION" key which receives an instruction input of connection confirmation, or the like may be displayed on the external terminal used by the user, as shown in FIG. 16, a light emitting unit 19, such as a light emitting diode (LED) may be provided in the housing 12 of each imaging device body 10, and when a "CONNECTION CONFIRMATION" key in the external terminal is depressed by the user, the light emitting unit 19 provided in the imaging device body 10 used by the user may be turned on or turned on and off. With this, the user can specify an imaging device to be used from among a plurality of imaging devices. The reception of the instruction input of connection confirmation by the external terminal is recognized by the terminal recognition unit 114 shown in FIG. 4, and the light emission of the light emitting unit 19 is controlled by the control unit 116.

What is claimed is:

1. An imaging device which photoelectrically reads fluorescence or chemiluminescence emitted from an object to image the object, the imaging device comprising:
   a control unit which receives first control information for controlling a first function and second control information for controlling a second function from a plurality of external terminals and performs the first function and the second function based on the received first and second control information; and
   a terminal recognition unit which recognizes the plurality of external terminals,
   wherein the control unit recognizes which external terminal output the first control information and the second control information by which the first function and the second function are executed based on the first and second control information output from each external terminal, sends a signal for prohibiting a reception of an operation instruction input of the first function to external terminals other than the external terminal that output the first control information, and performs parallel processing of the first function and the second function by the plurality of external terminals, and
   wherein the first function is an imaging function and the second function is an analysis function of an image acquired by imaging.

2. The imaging device according to claim 1,
   wherein
   when transferring an image captured by the imaging function from the imaging device to the external terminal, during a period of transfer, the control unit interrupts an execution of the analysis function.

3. The imaging device according to claim 1, wherein the control unit receives third control information for controlling a file operation function as a third function from each external terminal, recognizes the execution states of the first function and the third function by each external terminal, and performs parallel processing of the first function and the third function by the plurality of external terminals.

4. The imaging device according to claim 2, wherein the control unit receives third control information for controlling a file operation function as a third function from each external terminal, recognizes the execution states of the first function and the third function by each external terminal, and performs parallel processing of the first function and the third function by the plurality of external terminals.

5. The imaging device according to claim 1, wherein the control unit performs control such that only a function which is not controlled by other external terminals is executable by each external terminal.

6. The imaging device according to claim 2, wherein the control unit performs control such that only a function which is not controlled by other external terminals is executable by each external terminal.

7. The imaging device according to claim 3, wherein the control unit performs control such that only a function which is not controlled by other external terminals is executable by each external terminal.

8. The imaging device according to claim 1, wherein the control unit outputs information representing the execution states of the functions of the imaging device by other external terminals to each external terminal.

9. The imaging device according to claim 2, wherein the control unit outputs information representing the execution states of the functions of the imaging device by other external terminals to each external terminal.

10. The imaging device according to claim 3, wherein the control unit outputs information representing the execution states of the functions of the imaging device by other external terminals to each external terminal.

11. The imaging device according to claim 4, wherein the control unit outputs information representing the execution states of the functions of the imaging device by other external terminals to each external terminal.

12. The imaging device according to claim 5, wherein the control unit outputs information representing the execution states of the functions of the imaging device by other external terminals to each external terminal.

13. The imaging device according to claim 1, wherein the control unit receives execution reservation information of the first function from external terminals other than an external terminal, by which the first function is executed, and executes the first function in the order of reception of the execution reservation information.

14. The imaging device according to claim 2, wherein the control unit receives execution reservation information of the first function from external terminals other than an external terminal, by which the first function is executed, and executes the first function in the order of reception of the execution reservation information.

15. The imaging device according to claim 3, wherein the control unit receives execution reservation information of the first function from external terminals other than an external terminal, by which the first function is executed, and executes the first function in the order of reception of the execution reservation information.

16. A control method for the imaging device according to claim 1 which photoelectrically reads fluorescence or chemiluminescence emitted from an object to image the object, the control method comprising:
when receiving first control information for controlling a first function of the imaging device and second control information for controlling a second function of the imaging device from a plurality of external terminals and performing control of the imaging device based on the received first and second control information,
recognizing the execution states of the first function and the second function by each external terminal based on the first and second control information output from each external terminal; and
restricting simultaneous processing of the first function by the plurality of external terminals and performing parallel processing of the first function and the second function by the plurality of external terminals.

17. An imaging system comprising:
the imaging device according to claim 1; and
the plurality of external terminals,
wherein each external terminal includes an imaging device recognition unit which recognizes the imaging device and acquires execution information of the functions of the imaging device from the imaging device.

18. The imaging system according to claim 17, wherein a plurality of imaging devices are provided, each external terminal includes an imaging device information storage unit which stores registration information of the plurality of imaging devices, and the imaging device recognition unit recognizes the plurality of imaging devices based on the registration information and acquires the execution information of the functions of each imaging device.

19. The imaging system according to claim 17, wherein each external terminal includes a display control unit which displays information of the execution states of the functions of the imaging device.

20. The imaging system according to claim 19, wherein, when the first function of the imaging device is being executed, the display control unit of each of external terminals other than the external terminal, by which the first function is being executed, displays information indicating that the first function is being executed.

21. The imaging device according to claim 1, wherein the control unit sends a signal for prohibiting only a reception of an operation instruction input of the first function to external terminals other than the external terminal that output the first control information.

* * * * *